(12) United States Patent
Inazawa et al.

(10) Patent No.: US 8,741,641 B2
(45) Date of Patent: Jun. 3, 2014

(54) METHODS FOR EVALUATING THE STAGE OF OVARIAN CANCER OR THE SURVIVAL RATE OF AN OVARIAN CANCER PATIENT

(71) Applicants: Fujifilm Corporation, Tokyo (JP); National University Corporation Tokyo Medical and Dental University, Tokyo (JP)

(72) Inventors: Johji Inazawa, Tokyo (JP); Issei Imoto, Tokyo (JP); Ryoko Kikuchi, Tokyo (JP)

(73) Assignees: FUJIFILM Corporation, Tokyo (JP); National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 13/659,834

(22) Filed: Oct. 24, 2012

(65) Prior Publication Data

US 2013/0045479 A1 Feb. 21, 2013

Related U.S. Application Data

(62) Division of application No. 12/153,967, filed on May 28, 2008, now Pat. No. 8,318,431.

(30) Foreign Application Priority Data

May 30, 2007 (JP) .................................. 2007-143111

(51) Int. Cl.
*C12N 15/63* (2006.01)
*C12N 5/00* (2006.01)
*C12N 5/071* (2010.01)

(52) U.S. Cl.
CPC *C12N 15/63* (2013.01); *C12N 5/00* (2013.01); *C12N 5/0682* (2013.01)
USPC ............ 435/375; 435/325; 435/366; 435/455

(58) Field of Classification Search
CPC ... C12N 2501/10; C12N 5/0682; C12N 15/63
See application file for complete search history.

(56) References Cited

U.S. PATENT DOCUMENTS

| | | |
|---|---|---|
| 2004/0248206 A1 | 12/2004 | Lin et al. |
| 2005/0147986 A1 | 7/2005 | Kuo et al. |
| 2005/0181374 A1 | 8/2005 | Friedman et al. |
| 2007/0020692 A1 | 1/2007 | Weitz et al. |
| 2007/0054268 A1 | 3/2007 | Sutherland et al. |
| 2009/0004687 A1 | 1/2009 | Mansfield et al. |

FOREIGN PATENT DOCUMENTS

| | | |
|---|---|---|
| EP | 1 092 783 A1 | 4/2001 |
| TW | 200523547 A | 7/2005 |
| WO | WO 2006/050573 A1 | 5/2006 |

OTHER PUBLICATIONS

Helou et al., "Comparative genome hybridization reveals specific genomic imbalances during the genesis from benign through borderline to malignant ovarian tumors", Cancer Genetics and Cytogenetics, vol. 170, No. 1, pp. 1-8, Oct. 2006.
Hiroshi et al., "Identification of DNA copy number changes in microdissected serous ovarian cancer tissue using a cDNA microarray platform", Cancer Genetics and Cytogenetics, vol. 155, No. 2, pp. 97-107, Dec. 2004.
Jemal et al., "Cancer Statistics, 2006", CA Cancer J. Clin., vol. 56, No. 2, pp. 106-130, 2006.
Keiichi Hishikawa, et al., "Connective Tissue Growth Factor Induces Apoptosis in Human Breast Cancer Cell Line MCF-7", The Journal of Biological Chemistry, Dec. 24, 1999, vol. 274, No. 52, pp. 37461-37466, The American Society for Biochemistry and Molecular Biology, Inc., XP0029666506.
Norifumi H. Moritani, et al., "Suppressive effect of overexpressed connective tissue growth factor on tumor cell growth in a human oral squamous cell carcinoma-derived cell line", Cancer Letters, Mar. 31, 2003, vol. 192, No. 2, pp. 205-214, Elsevier Science Ireland Ltd., XP002509416.
Ozols et al., "Focus on Epithelial Ovarian Cancer", Cancer Cell, vol. 5, pp. 19-24, 2004.
Ryoko, Kikuchi, et al., "Promotor Hypermethylation Contributes to Frequent Inactivation of a Putative Conditional Tumor Suppressor Gene Connective Tissue Growth Factor in Ovarian Cancer", Cancer Research, Aug. 1, 2007, vol. 67, No. 15, pp. 7095-7105, XP002509417.
Tojo et al., "Expression of the GLI2 oncogene and its isoforma in human basal cell carcinoma", British Journal of Dermatology, vol. 148, No. 5, pp. 892-897, May 2003.
Wasenius et al., "Comparative genomic hybridzation analysis of chromosomal changes occurring during development of acquired resistance to cisplatin in human ovarian carcinoma cells", Genes, Chromosomes & Cancer, vol. 18, No. 4, pp. 286-291, (1997).
Sigal Gery, et al., "Ovarian Carcinomas: CCN Genes Are Aberrantly Expressed and CCN1 Promotes Proliferation of These Cells," Clin. Cancer Res., 2005, vol. 11, No. 20, pp. 7243-7254.

*Primary Examiner* — Marianne P Allen
(74) *Attorney, Agent, or Firm* — Birch, Stewart, Kolasch & Birch, LLP

(57) ABSTRACT

An object of the present invention is to provide a method for detecting cancer through identification of genes exhibiting characteristic behavior in the cases of cancer such as ovarian cancer, and a cell growth inhibitor. The present invention provides a method for detecting cancer, which comprises detecting canceration including malignancy of a specimen through detection of at least one alteration of a gene existing in a chromosomal region 2q14. 2, 3p24. 1, 3q26. 2, 3q29, 4q34. 2, 6q23, 9p21. 3, 11q13. 3, 13q22.1, 13q33. 1, 13q33. 3, 15q12, 15q15. 1, 17p12, 17p13. 1, 17p13. 3, 18q21. 1, 18q21. 2, 18q21. 31, 18q21. 32, 18q21. 33, 18q23, 20q13. 13, 20q13. 2, 20q13. 31, 20q13. 33, Xp11. 23, Xp13.1, Xp13. 3, Xp26. 2, Xp26. 3, or Xq28 in the specimen.

2 Claims, 4 Drawing Sheets

SEQUENCE LISTING

<160> NUMBER OF SEQ ID NOS: 48

<210> SEQ ID NO 1
<211> LENGTH: 20
<212> TYPE: DNA
<213> ORGANISM: Artificial Sequence

```
<220> FEATURE:
<223> OTHER INFORMATION: Description of Artificial Sequence: Synthetic
      DNA

<400> SEQUENCE: 1
ttccagagca gctgcaagta                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
aaggaaggaa aggcacacaa                                                    20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
gcatggaaca aggcagttg                                                     19

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
aggagcacta atttattctg ataaaac                                            27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
agggaacgct ccaggtaaag                                                    20

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
ttccctcttg gtgtaaaatt caa                                                23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
```

DNA

<400> SEQUENCE: 7
cttgcagcgt gctgtttaag                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
tcacacaggt ttgaggatgc                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
atgaaacgtt tttgcccttg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
agagcgctgt ctcaggtcat                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
ttccagagca gctgcaagta                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
cagatcatgg catggaacaa                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 13
gcagctacca ggacaatgga                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
ggcaaacttc cacactggtt                                                  20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
tcaggatgac tgtggaatca ct                                               22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
ggggaagatt aagtaagaaa gtca                                             24

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
cagctggtgt gtgctagaag ag                                               22

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
gtaggaaggt ggggaggaa                                                   19

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
```

```
ggaatgttga gtgttaaggg gttaggatta                                  30
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20

```
ttgagaggag atagttagtg                                             20
```

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21

```
ggttgttagg gagggatt                                               18
```

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22

```
gtataagggt ttattttgtt attt                                        24
```

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23

```
gggtcgtgtc ggtgttc                                                17
```

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24

```
gttgtgttgg tgtttggat                                              19
```

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25

```
ctcgtcacac acccactcc                                              19
```

```
<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
tttccaaggg gctggagtat                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
gggacatcag agggtctcaa                                                   20

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
gtgttcttct taacaggttg ttcc                                              24

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
cctcttcgaa aatgctctgc                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
gggggcttat gtaagtgtgc                                                   20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
tgggccattc ttctttcatc                                                   20

<210> SEQ ID NO 32
```

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
tagggtcaaa ggcaaaggaa                                                 20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
acctttccca aacctttgct                                                 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
aatccttcca aaacggaggt                                                 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
ccaggcagtt ggctctaatc                                                 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
gggacatcag agggtctcaa                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
gcaagaagaa caatgcaagc                                                 20

<210> SEQ ID NO 38
<211> LENGTH: 20
<212> TYPE: DNA
```

<213> ORGANISM: Artificial Sequence
<220> FEATURE:
<223> OTHER INFORMATION: Description of Artificial Sequence: Synthetic
      DNA

<400> SEQUENCE: 38
atccctggaa taaggctgct                                           20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
tgaaaggaac catcactgac c                                         21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
aggtttggtg ttggcatttt                                           20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
ccacgaacaa ccacaacatc                                           20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
cactaactat ctcctctcaa c                                         21

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
atcaaacatt aaaacactct cacatccaaa                                30

<210> SEQ ID NO 44
<211> LENGTH: 20
<212> TYPE: DNA
<213> ORGANISM: Artificial Sequence
<220> FEATURE:

```
<223> OTHER INFORMATION: Description of Artificial Sequence: Synthetic
      DNA

<400> SEQUENCE: 44
aacaaaataa acccttatac                                                      20

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
tccatactac acaaaaacat acaacc                                               26

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
gtataagggt ttattttgtt attt                                                 24

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
gtccaacacg aaactcacg                                                       19

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
catccaacac aaaactcaca                                                      20
```

METHODS FOR EVALUATING THE STAGE OF OVARIAN CANCER OR THE SURVIVAL RATE OF AN OVARIAN CANCER PATIENT

This application is a Divisional of co-pending application Ser. No. 12/153,967 filed on May 28, 2008 and for which priority is claimed under 35 U.S.C. §120. This application also claims priority under 35 U.S.C. §119 of Application No. 2007-143111 filed in Japan on May 30, 2007. The entire contents of each of the above-identified applications are hereby incorporated by reference.

TECHNICAL FIELD

The present invention relates to a method for detecting cancer by detecting gene alterations that exist in specific chromosomal regions for the purpose of early diagnosis of ovarian cancer through observation of the genotype thereof.

BACKGROUND ART

Ovarian cancer (OC) occurs most frequently in 50-to-70-year-old females and is the second most common form of cancer among gynecologic cancers. The ovarian cancer mortality rate is known to be higher than that of other gynecologic cancers. Various types of ovarian cancer exist, and they develop separately from different types of cells in the ovary. Epithelial cancer, which is developed on the ovarian surface, accounts for about 80% or more of ovarian cancer cases.

In recent years, although procedures for diagnosis and treatment for ovarian cancer have been advanced, the early diagnosis thereof has remained difficult to make. Accordingly, it has been desired to discover a causative gene for ovarian cancer and to elucidate the functions for establishment of new strategic understandings for effective therapeutic methods, search for diagnostic markers and chemical prevention.

DISCLOSURE OF THE INVENTION

Successful elucidation of the mechanism of canceration of ovary-derived cells and mainly ovarian epithelium-derived cells at the gene level will enable detection of canceration of ovary-derived cells at the gene level, diagnosis of the malignancy of ovarian cancer, and suppression of the advancement thereof. Furthermore, it will also enable establishment of methods for selecting and developing drugs, as well as therapeutic methods based on such mechanisms. Specifically, this object can be achieved by identifying genes exhibiting characteristic behavior observed in ovarian cancer cases and then carrying out technical examination mainly targeting such genes. Hence, an object to be achieved by the present invention is to provide a method for detecting cancer through identification of genes exhibiting characteristic behavior in the cases of cancer such as ovarian cancer, and a cell growth inhibitor.

Comparative Genomic Hybridization (CGH) is the best method for conveniently and rapidly analyzing genetic abnormalities accompanying amplification or deletion of numerous genes in the genome or inactivation of genes. To analyze genetic abnormalities in the genome involved in canceration and higher cancer malignancy, the present inventors have selected 800 types of BAC/PAC DNA to be subjected to CGH array (MCG CancerArray-800; Takada H., et al., Cancer Sci. 96, 100-105, 2005). As a result, the present inventors have succeeded in identification of a cancer-associated gene that promotes canceration of ovary-derived cells; that is, Connective tissue growth factor (CTGF) gene. Moreover, the present inventors have succeeded in discovering that deletion or inactivation of the CTGF gene, and specifically a decrease in the CTGF protein, significantly promote the proliferation of ovarian cancer and that the increased level of a transcript or the protein of the CTGF gene results in significantly decreased levels of ovarian cancer proliferation. Thus, the present inventors have completed the present invention.

The present invention provides a method for detecting cancer, which comprises detecting canceration including malignancy of a specimen through detection of at least one alteration of a gene existing in a chromosomal region 2q14. 2, 3p24. 1, 3q26. 2, 3q29, 4q34. 2, 6q23, 9p21. 3, 11q13. 3, 13q22.1, 13q33. 1, 13q33. 3, 15q12, 15q15. 1, 17p12, 17p13. 1, 17p13. 3, 18q21. 1, 18q21. 2, 18q21. 31, 18q21. 32, 18q21. 33, 18q23, 20q13. 13, 20q13. 2, 20q13. 31, 20q13. 33, Xp11. 23, Xp13.1, Xp13. 3, Xp26. 2, Xp26. 3, or Xq28 in the specimen.

Preferably, the gene is at least one of GLI2, CCND1, FGF3, TGFBR2, CDKN2A, MTAP, SMAD4, EVI1, MUC4, PTPN1, ZNF217, BCAS1, TFAP2C, BIRC7, TNFRSF6B, VEGFC, KLF12, FGF14, EFNB2, GABRB3, RAD51, RH68621, PMP22, RCV1, HSXIAPAF1, ABR, HIC1, MADH4(SMAD4), DCC, MALT1, GRP, SERPINB5, FVT1, BCL2, SERPINB3, BCL2, CTDP1, SHGC-145820, SSX1, AR, MLLT7, ABCB7, GPC3, FGF13, MAGEA2, KIAA1913, EPB42L2, AKAP7, CRSP3, ARG1, ENPP3, ENPP1, and CTGF.

Preferably, the gene alteration is at least one of amplification, deletion, and inactivation.

Preferably, the gene alteration is inactivation due to methylation of a CpG island.

Preferably, canceration including malignancy of a specimen is detected through detection of the amount of the protein that is translated from the gene according to claim 2 in the specimen.

Preferably, the amount of the protein is detected by an immunohistochemical method.

Preferably, canceration including malignancy of a specimen is detected through detection of deletion or inactivation of a CTGF gene.

Preferably, the specimen is tissue derived from the ovary.

Preferably, the cancer is ovarian cancer.

Preferably, the gene alteration is detected using a DNA chip method, a Southern blot method, a Northern blot method, a real-time RT-PCR method, a FISH method, a CGH method, an array CGH method, a bisulfite sequencing method, or a COBRA method.

The present invention further provides a method for inhibiting cell growth, which comprises introducing a KIAA1913, EPB42L2, AKAP7, CRSP3, ARG1, ENPP3, ENPP1, or CTGF gene, or a protein that is an expression product thereof into cells in vitro.

The present invention further provides a cell growth inhibitor, which comprises a KIAA1913, EPB42L2, AKAP7, CRSP3, ARG1, ENPP3, ENPP1, or CTGF gene, or a protein that is an expression product thereof.

The present invention further provides a method for activating cell growth, which comprises introducing siRNA, shRNA, an antisense oligonucleotide, or a loss-of-function type gene of a KIAA1913, EPB42L2, AKAP7, CRSP3, ARG1, ENPP3, ENPP1, or CTGF gene into tumor cells in vitro.

The present invention further provides a cell growth activating agent, which comprises siRNA, shRNA, an antisense oligonucleotide, or a loss-of-function type gene of a KIAA1913, EPB42L2, AKAP7, CRSP3, ARG1, ENPP3, ENPP1, or CTGF gene.

The present invention further provides a method for screening for a substance, which comprises causing a test substance to come into contact with ovarian cancer in which gene expression is suppressed due to methylation of a CpG island of a KIAA1913, EPB42L2, AKAP7, CRSP3, ARG1, ENPP3, ENPP1, or CTGF gene, detecting the expression of the gene, and then selecting a test substance as an anti-tumor substance capable of activating the relevant gene by demethylation of the CpG island of the gene when the gene expression is increased to a level higher than that in a system in which the test substance is not caused to come into contact therewith.

B: Confirmation of the amplification of the 6q23.2 chromosomal region in ovarian cancer cell lines.

Upper; Array CGH image representing the typical amplification of the RMUG-S cell line. Homozygous deletion of the BAC clone in the 6q23.2 chromosomal region could be confirmed with a clear signal (arrow).

Lower; Map covering 6q23.1-23.2 homozygous deletion regions in the RMUG-S cell line. BAC (RP11-6918) indicated with a horizontal line has homozygous deletion as revealed by array CGH analysis. Homozygous deletion regions in the RMUG-S cell line were each determined by genomic PCR and indicated with a white left-right arrow. In the RMUG-S cell line, 10 genes located in the periphery of the homozygous deletion region determined by genomic PCR, homozygously-deleted genes (8 genes), or the remaining genes (2 genes) are indicated with arrows.

C: Genomic PCR and RT-PCR analysis of genes located in the periphery of the 6q23 homozygous deletion region in ovarian cancer cell lines Upper; Homozygous deletion of CTGF, ENPP1, ENPP3, CRSP3, ARG1, AKAP7, EPB41L2, and KIAA1913 could be confirmed by genomic PCR in one ovarian cancer cell line.

1: HT, 2: HTOA, 3: HUOA, 4:KF28, 5: MH, 6:OVKATE, 7: OVSAHO, 8: KFr13, 9: HMKOA, 10: MCAS, 11: RMUG-L, 12: RMUG-S, 13:KK, 14: OVISE, 15: OVMANA, 16: OVTOKO, 17: RMG-I, 18:RMG-II, 19: ES-2, 20: W3UF, 21: HIOAnu, 22: HMOA, 23: HNOA, and 24: HTBOA.

Lower; The mRNA expression of CTGF, ENPP1, ENPP3, CRSP3, AKAP7, EPB41L2, and KIAA1913 in an ovarian cancer cell line, normal ovary, and a normal ovarian epithelium cell-derived cell line (OSE-2a) were confirmed by RT-PCR. An arrowhead indicates a cell line that exhibited homozygous deletion as revealed by genomic PCR analysis. Slightly decreased mRNA expression levels of CRSP3, AKAP7, and EPB41L2 were shown in many ovarian cancer cell lines. The mRNA expression of ENPP1, ENPP3, and CTGF disappeared frequently. Decreased CTGF gene expression levels due to reasons other than homozygous deletion were confirmed in 12 (types) out of 23 cell lines (50%).

D: Ovarian cancer cell lines (HNOA and RMG-I) were treated (+) or not treated (−) with 5-aza-dCyd (5 μM) for 5 days or TSA (100 ng/ml) for 12 hours. The results of RT-PCR analysis on the CTGF gene in the ovarian cancer cell lines.

Figure 2:
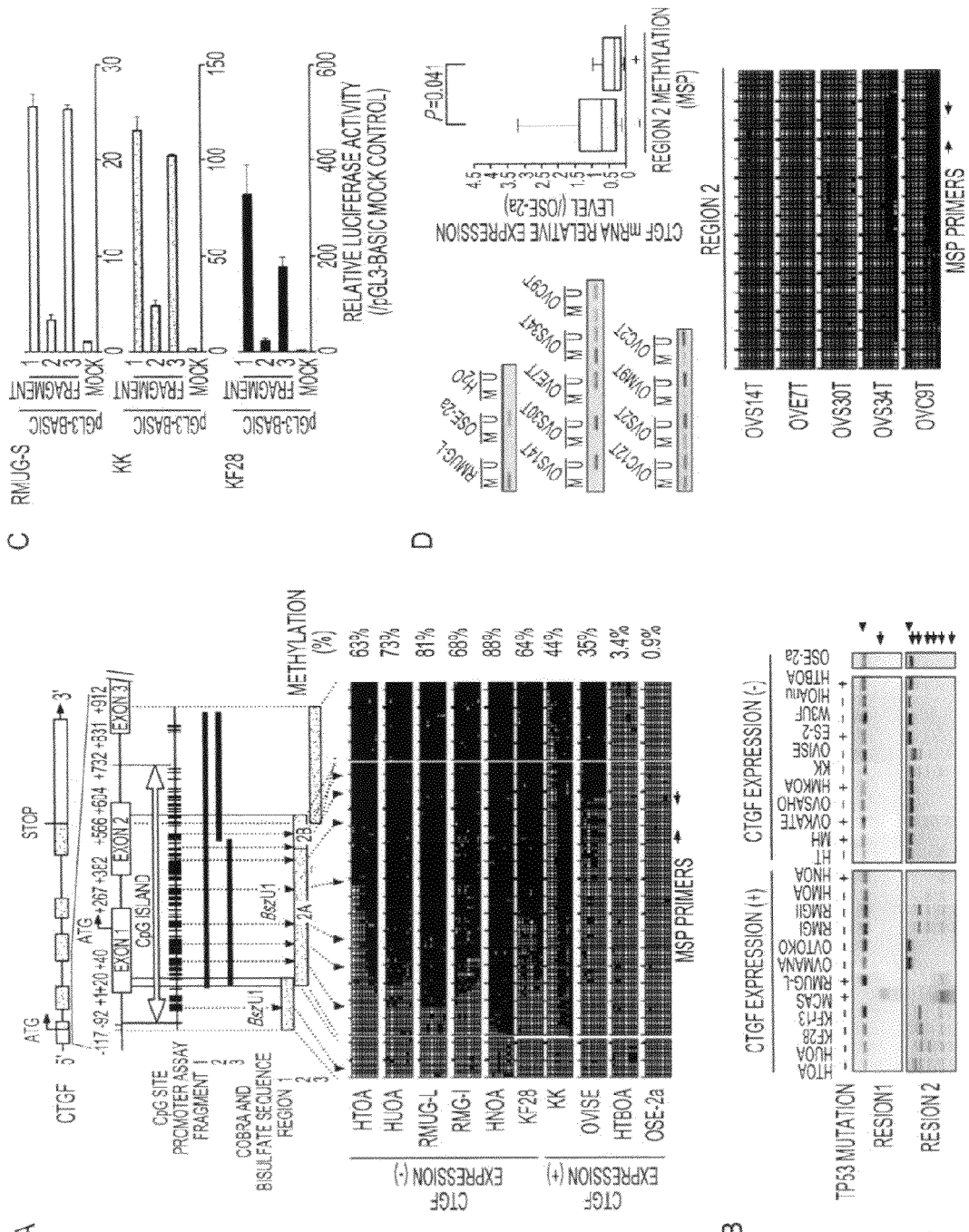

FIG. 2 shows methylation status of the CTGF CpG-rich region in ovarian cancer cell lines and clinical ovarian cancer specimens A: Schematic view of the CpG rich region including the CpG island (white arrow) in the periphery of exon 1 of the CTGF gene, and typical results of bisulfite sequencing. A vertical line represents the CpG site. An open box represents exon 1. The transcription initiation site is indicated with "+1." Thick black lines represent fragments used for promoter assay. A gray line represents a region confirmed by the COBRA method and bisulfite sequencing. A black arrowhead represents a restriction enzyme site BstU 1 for the COBRA method.

Typical results of bisulfite sequencing of a CpG rich region, which was examined in an ovarian cancer cell line (+) expressing CTGF and an ovarian cancer cell line (−) not expressing CTGF. Each white square represents an unmethylated CpG site and each black square represents a methylated CpG site. Each column represents the one derived from 1 type of clone. PCR primers for MSP are indicated with arrows.

B: Typical results of performing the COBRA method for the CTGF CpG island in ovarian cancer cell lines after digestion thereof with BstU I. An arrow indicates a fragment that was digested specifically to a methylated CpG site. An arrowhead indicates a fragment that is not digested and an unmethylated CpG.

C: Promoter activity of the CTGF CpG rich region. A pGL3 empty vector (mock) and reporters containing different sequences of CpG island fragments 1-3 were constructed. RMUG-S, KK, and KF28 cells were transfected with them together with an internal control vector (pRL-hTK). Luciferase activity was normalized with respect to the control. Data indicate average±SD of values obtained via three independent experiments.

D: Upper left; Typical results of MSP analysis performed for the CTGF promoter region in clinical ovarian cancer specimens. Examination was performed using primers specific to unmethylated (U) or methylated (M) DNA.

Lower; Methylation status of the CTGF promoter region in tumor samples was determined by bisulfite sequencing.

Upper right; Correlation between CTGF methylation status determined by MSP and CTGF mRNA expression status determined by RT-PCR in 43 types of clinical ovarian cancer (other than mucinous tumor) specimen.

Figure 3:
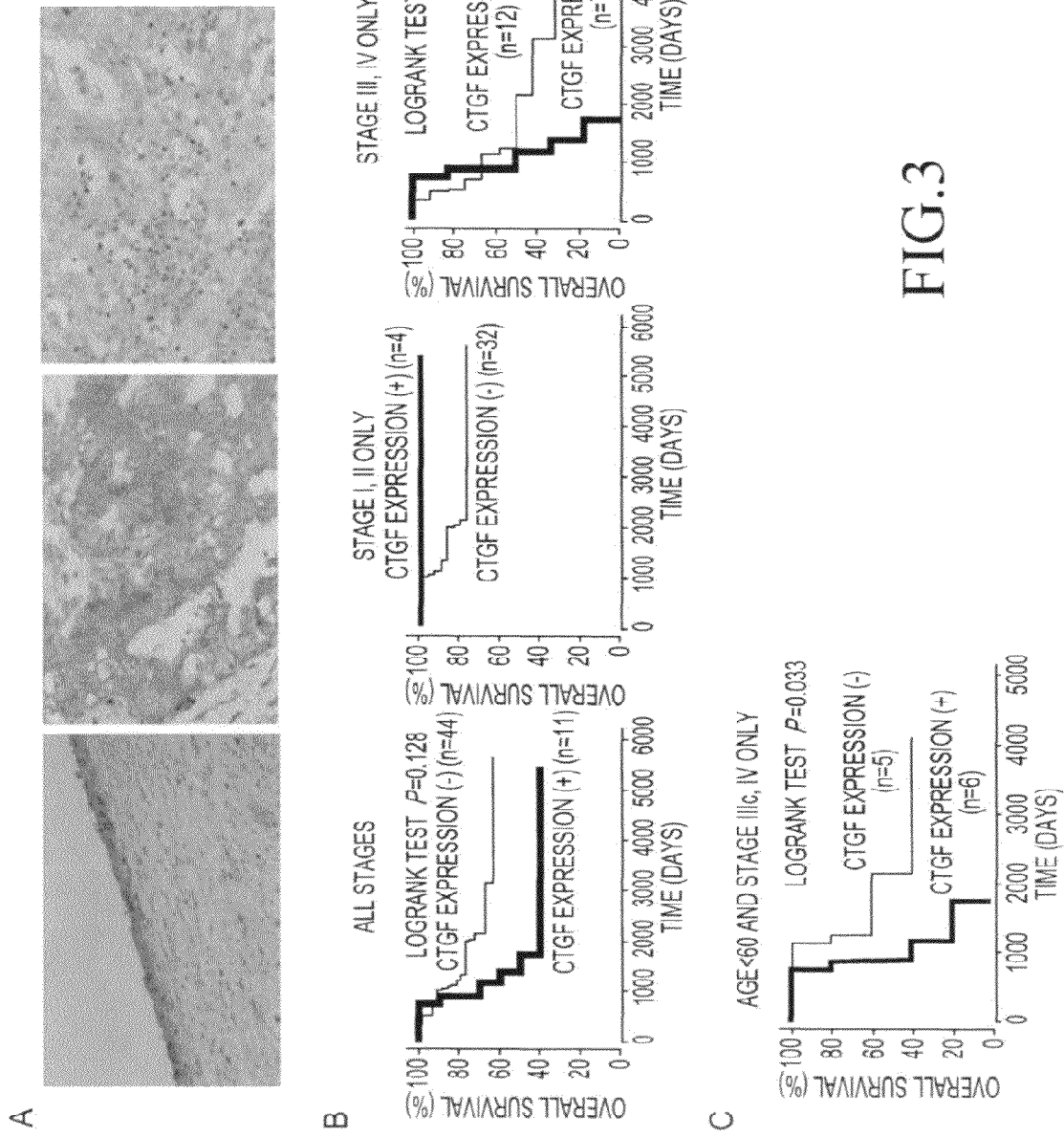

FIG. 3 shows immunohistochemical analysis of CTGF expression in clinical ovarian cancer specimens.

A: Typical CTGF immunochemical staining in normal human ovarian epithelial cells and clinical ovarian cancer specimens. Left; High CTGF expression was observed in normal ovarian epithelial cells. Center and right; High CTGF expression (center) or almost no CTGF expression (right) was observed in cancer cells of clinical ovarian cancer specimens. CTGF was clearly localized at the apex of the cytoplasm in normal epithelial cells and ovarian cancer cells. Magnification ×200.

B: Kaplan-Meier curve with respect to the overall survival rate of ovarian cancer patients. Left; In the cases of tumors at all stages, the survival rates of patients who were confirmed by an immunohistochemical method to exhibit low CTGF expression levels were better than those of patients found to exhibit high CTGF expression levels (P=0.128, Log-rank test). Center; In the cases of tumors at stages I and II, statistical analysis cannot be conducted since no death was confirmed in a group of patients with high CTGF expression levels. It is shown that patients with low CTGF expression levels tended to have lower survival rates than those of patients with high CTGF expression levels. Right; In the cases of tumors at stages III and IV, it is shown that the survival rates of patients with high CTGF expression levels were lower than those of patients with low CTGF expression levels (P=0.189, Log-rank test).

C: Kaplan-Meier curve with respect to the overall survival rate of ovarian cancer patients at stages IIIc and IV under the age of 60 or less. When subject patients were limited to ovarian cancer patients at stages IIIc and IV associated with metastatic phenotype under the age of 60 or less, it is shown that the survival rates of patients with high CTGF expression levels were clearly lower than those of patients with low CTGF expression levels although only few such cases were analyzed (P=0.033, Log-rank test).

Figure 4:
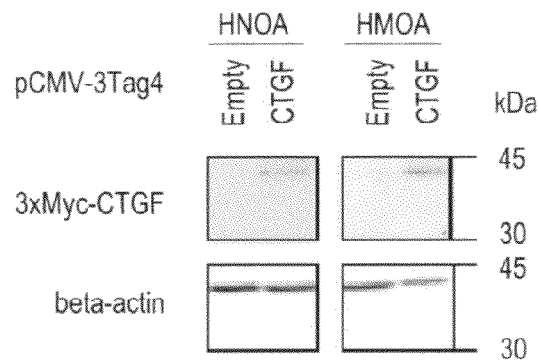
Figure 4:
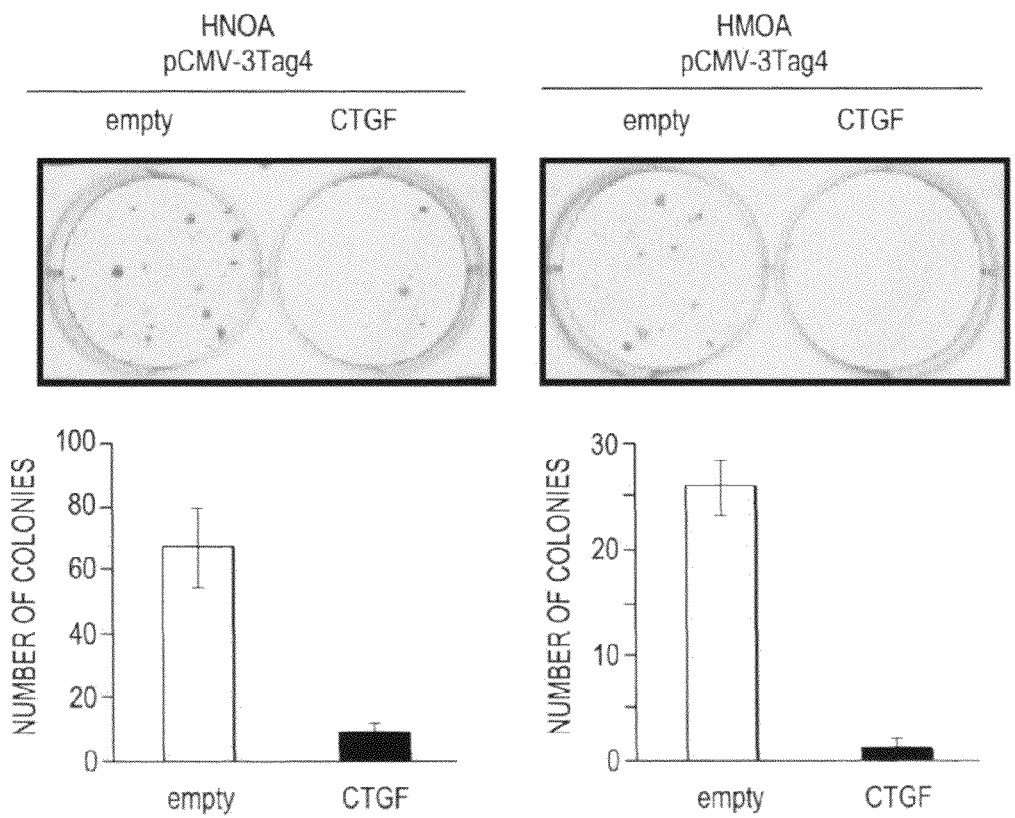

FIG. 4 shows effects of CTGF expression on the proliferation of ovarian cancer (A and B). Cell lines (HNOA and HMOA) lacking the CTGF gene were transfected with pCMV-3Tag4-CTGF or pCMV-3Tag4-mock.

A: Western blot analysis was performed using 10 µg of protein extracted from cells at 48 hours after transfection and an anti-Myc antibody.

B: Colony formation assay using cell lines (HNOA and HMOA) not expressing the CTGF gene. These cells were transiently transfected with a Myc tag vector (pCMV-3Tag4-CTGF) containing CTGF or an empty vector (pCMV-3Tag4-mock), followed by 2 weeks of drug selection in the presence of G418.

Upper: Drug resistant colonies were formed within 2 weeks after transfection, revealing that the degree of colony formation by cells transfected with the CTGF gene was less than that by cells transfected with the empty vector.

Lower: Quantitative analysis of colony formation. Colonies (>2 mm) were counted. Counting was performed in 3 separate experiments. The result is represented by the average value±SD of three separate results.

PREFERRED EMBODIMENTS OF THE INVENTION

Hereafter, the present invention is described in detail.
(1) Method for Detecting Cancer The method for detecting cancer according to the present invention comprises detecting canceration including the malignancy of a specimen, through detection of at least one alteration of a gene existing in chromosomal region 2q14.2, 3p24.1, 3q26.2, 3q29, 4q34.2, 6q23, 9p21.3, 11q13.3, 13q22.1, 13q33.1, 13q33.3, 15q12, 15q15.1, 17p12, 17p13.1, 17p13.3, 18q21.1, 18q21.2, 18q21.31, 18q21.32, 18q21.33, 18q23, 20q13.13, 20q13.2, 20q13.31, 20q13.33, Xp11.23, Xp13.1, Xp13.3, Xp26.2, Xp26.3, or Xq28 in the specimen. As the above gene, at least one of GLI2, CCND1, FGF3, TGFBR2, CDKN2A, MTAP, SMAD4, EVI1, MUC4, PTPN1, ZNF217, BCAS1, TFAP2C, BIRC7, TNFRSF6B, VEGFC, KLF12, FGF14, EFNB2, GABRB3, RAD51, RH68621, PMP22, RCV1, HSXIAPAF1, ABR, HIC1, MADH4(SMAD4), DCC, MALT1, GRP, SERPINB5, FVT1, BCL2, SERPINB3, BCL2, CTDP1, SHGC-145820, SSX1, AR, MLLT7, ABCB7, GPC3, FGF13, MAGEA2, KIAA1913, EPB42L2, AKAP7, CRSP3, ARG1, ENPP3, ENPP1, and CTGF can be selected. Particularly preferably, canceration including malignancy of specimen can be detected through detection of deletion or inactivation of CTGF gene in ovary-derived cells.

As a result of the human genome project, transcripts of the CTGF gene are already known. The gene is located on chromosomal region 6q23. Protein encoded by the CTGF gene belongs to CCN (CTGF, CYR61, NOV) family, and is known to be widely involved in biochemical and pathological processes such as angiogenesis, osteogenesis, kidney diseases and skin diseases, but the detailed functions thereof remains unknown. The fact that the CTGF gene is an important cancer-associated gene involved in the onset of ovarian cancer or the malignancy thereof was unknown before the present invention.

As described above, the detection method comprises detecting deletion or inactivation of CTGF gene in ovary-derived cells or ovarian cancer.

Preferred examples of ovary-derived cells or ovarian cancer to be subjected to detection of deletion or inactivation of the CTGF gene are biopsied tissue cells of specimen donors.

Such tissue cell specimen may be an ovary-derived cell of a healthy subject or a cancerous tissue of an ovarian cancer patient. In practice, examples of a major target tissue specimen that can be used herein include: a tissue obtained from a lesion in which suspected canceration of the ovary is observed by a test or the like; and an ovarian tissue that has been confirmed to be derived from ovarian cancer and thus must be subjected to determination of malignancy or the stage progression of ovarian cancer.

In a case in which the deletion or inactivation of the CTGF gene is observed in "a tissue obtained from a lesion in which suspected canceration of the ovary is observed by a test or the like" by the detection method of the present invention, it is understood that such lesion tissue will reach (or has reached) the state of canceration so that the level of malignancy of the disease will increase. Thus, there is a demonstrated urgent need for implementation of a full-scale therapy (e.g., elimination of a lesion via a surgery or the like and full-scale chemotherapy). In addition, in a case in which the deletion or inactivation of the CTGF gene is observed in "an ovarian tissue that has been confirmed to be derived from ovarian cancer and thus must be subjected to determination of malignancy or the stage progression of ovarian cancer," it is also understood that the level of malignancy of the cancerous tissue will increase. Thus, there is a demonstrated urgent need for implementation of full-scale therapy (e.g., elimination of a lesion via a surgery or the like and full-scale chemotherapy). An ovarian cancer tissue collected as a specimen may be subjected to necessary treatment such as preparation of DNA or RNA from the collected tissue followed by the detection method of the present invention.

(2) Detection of Deletion of CTGF Gene

Examples of a typical method by which CTGF gene deletion can be directly detected include a CGH (Comparative Genomic Hybridization) method and a FISH (Fluorescence in situ hybridization) method. According to the detection method in this embodiment, BAC (Bacterial Artificial Chromosome) DNA, YAC (Yeast Artificial Chromosome) DNA, or PAC (P1-drived Artificial Chromosome) DNA (hereinafter, also referred to as BAC DNA, for example) having the CTGF gene is labeled and then FISH is performed, so that the presence or the absence of the CTGF gene (that is, deletion of CTGF gene) can be detected. Specific examples of such BAC DNA having the CTGF gene include RP11-69I8 and the like.

It is preferable and practical to carry out the method in the above embodiment with the use of a genomic DNA-immobilized matrix.

The amount of BAC DNA or the like obtained in a conventional manner is so small that a large number of genomic DNA-immobilized matrices cannot be produced for practical application. Thus, it is necessary to obtain gene amplification products of such DNA. (A gene amplification process for this purpose is referred to as "infinite amplification" in some cases.) Upon infinite amplification, BAC DNA or the like is first digested with a four-base recognition enzyme such as Rsa I, Dpn I, Hae III, or the like, followed by ligation with the addition of an adaptor. An adaptor comprises oligonucleotides having 10 to 30 bases and preferably 15 to 25 bases. Double strands of such adaptor have sequences complementary to each other. After annealing, the 3' end of one of the oligonucleotides, at which a blunt end is formed, must be phosphorylated. Next, a primer having a sequence identical to the other oligonucleotide of the adaptor is used for amplification via PCR (polymerase chain reaction). Thus, infinite amplification can be carried out. Meanwhile, it is also possible to use, as a detection probe, an aminated oligonucleotide comprising 50 to 70 bases, which is inherent to BAC DNA or the like.

BAC DNAs or the like subjected to infinite amplification are immobilized on a matrix and preferably on a solid matrix. Accordingly, a desired DNA-immobilized matrix can be produced. An example of such solid matrix is more preferably a glass plate. Such a solid matrix made of glass or the like is more preferably coated via adhesion with poly-L-lysine, aminosilane, gold, aluminium, or the like.

The concentration of DNA subjected to infinite amplification to be spotted on a matrix is preferably 10 pg/µl to 5 µg/µl and more preferably 1 ng/µl to 200 ng/µl. The amount of the same to be spotted on the matrix is preferably 1 nl to 1 µl and more preferably 10 nl to 100 nl. In addition, the size and the shape of each spot that is immobilized on the matrix are not particularly limited. In terms of size, such spot may have a diameter ranging from 0.01 to 1 mm, for example. In addition, the shape of such spot may be a circle or ellipse from an overhead view. The thickness of a dry spot is not particularly limited; however, it may be 1 to 100 µm. Further, the number of spots is not particularly limited; however, it may be 10 to 50,000 spots and more preferably 100 to 5,000 spots on the matrix used. DNAs are spotted singly to quadruplicate. However, preferably, DNAs are spotted in duplicate or triplicate.

Regarding preparation of dry spots, it is possible to produce dry spots by, for example, spotting BAC DNAs or the like subjected to infinite amplification on a matrix with the use of a spotter, forming a plurality of spots thereon, and drying the spots. Examples of a spotter that can be used include an inkjet printer, a pin-array printer, and a bubble jet (trademark) printer. An inkjet printer is desirably used. For instance, GENESHOT (NGK INSULATORS; Nagoya, Japan) or the like can be used.

As described above, it is possible to produce a desired DNA-immobilized matrix by immobilizing BAC DNAs or the like subjected to infinite amplification onto a matrix, and preferably, onto a solid matrix.

In addition, an example of a means of directly detecting the deletion of the CTGF gene is the Southern blot method. The Southern blot method is a method for detecting the presence of the CTGF gene in a specimen by separating and immobilizing genomic DNA obtained from the specimen and detecting hybridization of such genomic DNA with the CTGF gene.

Furthermore, the deletion of the CTGF gene can also be detected by the Northern blot method or the real-time RT-PCR method. The Northern blot method comprises separating and immobilizing mRNA obtained from a specimen and detecting hybridization between the mRNA and the CTGF gene, so as to detect the presence of the mRNA of the gene in the specimen. The real-time RT-PCR method is a method for determining (in realtime) the amplification of a target gene as a result of a reverse transcription reaction and a polymerase chain reaction. By such method, mRNA serving as a template can be determined based on amplification rate. The determination is carried out using a fluorescent dye. There are two known methods: a method involving specific insertion (intercalation) of a dye (e.g., SYBR green) emitting fluorescence into double-stranded DNA; and a method involving a probe prepared by binding a fluorescent dye to an oligonucleotide specific to a DNA sequence to be amplified.

(3) Detection of Inactivation of CTGF Gene

It has been reported that transcriptional inactivation occurs when a CpG-rich promoter and an exon region are densely methylated (Bird A P., et al., Cell, 99, 451-454, 1999). In the cases of cancer cells, CpG islands are frequently and densely methylated compared with other regions, and thus hypermethylation of a promoter region is deeply involved in the inactivation of an antioncogene of a cancer (Ehrlich M., et al, Oncogene, 21, 6694-6702, 2002).

As described below, CpG islands existing in an exon of the CTGF gene was actually found to have promoter activities. In addition, the extent of methylation of the CpG islands strongly correlated with suppression of the expression of the CTGF gene in some ovarian cancer cases.

In addition, it was possible to demethylate such CpG islands by culturing such ovarian cancer cells in the presence of 5-azadeoxycytidine (5-aza-dCyd) serving as a demethylating reagent. As a result, it was possible to recover the expression level of the CTGF gene. Based on the above results, it has been revealed that highly frequent methylation (hypermethylation) of CpG islands is a cause of frequently occurring suppression of the expression of an antioncogene in ovarian cancer.

Recovery of the CTGF gene expression level can be examined using the above detection means, specifically by causing a demethylating reagent (e.g., 5-azadeoxycytidine) to act on a cell specimen (a primary cancer cell derived from a cancerous tissue) that has been revealed to exhibit a decreased CTGF gene expression level. More specifically, when the expression level of the CTGF gene can be recovered by causing a demethylating reagent to act on a cell specimen, a factor that suppresses the gene in the cell specimen is methylation of CpG islands. Hence, a reasonable anti-tumor effect is expected with the administration of a drug having a demethylating effect to a specimen donor.

(4) Method for Inhibiting Cell Growth and Cell Growth Inhibitor

According to the present invention, there are further provided a method for inhibiting cell growth which comprises introducing a KIAA1913, EPB42L2, AKAP7, CRSP3, ARG1, ENPP3, ENPP1 or CTGF gene or a protein which is an expression product of such a gene into cells in vitro, and a cell growth inhibitor comprising said gene or protein.

For handling the KIAA1913, EPB42L2, AKAP7, CRSP3, ARG1, ENPP3, ENPP1 or CTGF gene, cDNAs obtained from cultured cells through publicly known methods to those skilled in the art may be used, or enzymatically synthesized ones through PCR method may be also used. When DNA is obtained through PCR method, PCR is performed using human chromosomal DNA or cDNA library as a template, and primers designed to amplify a nucleotide sequence of interest. DNA fragments amplified through PCR can be cloned in an appropriate vector which can proliferate in a host such as *E. coli*.

Manipulations such as preparation of detection probes or primers for the KIAA1913, EPB42L2, AKAP7, CRSP3, ARG1, ENPP3, ENPP1 or CTGF gene and cloning of target genes are already known to those skilled in the art. For example, such manipulations can be performed according to methods described in Molecular Cloning: A Laboratory Manual, $2^{nd}$ Ed., Cold Spring Harbor Laboratory, Cold Spring Harbor, N.Y., 1989, Current Protocols in Molecular Biology, Supplement 1 to 38, John Wiley & Sons (1987-1997), or the like.

The KIAA1913, EPB42L2, AKAP7, CRSP3, ARG1, ENPP3, ENPP1 or CTGF gene can be used in the form of a recombinant vector having such a gene incorporated therein. Examples of the vector to be used herein may include viral vectors and vectors for expression in animal cells. Preferably, viral vectors are used. Examples of such viral vector include retroviral vectors, adenoviral vectors, adeno-associated virus vectors, baculovirus vectors, vaccinia virus vectors, and lentivirus vectors. Of these, retroviral vectors are particularly preferred to use, since retroviral vectors enable stable and long-term expression of a foreign gene that had been incorporated into such vectors, through incorporation of the virus genome into a host chromosome after infection into cells.

Examples of the vector for expression in animal cells to be used herein may include pCXN2 (Gene, 108, 193-200, 1991), PAGE207 (JP Patent Publication (Kokai) No. 6-46841 (1994)) or variants thereof.

The above recombinant vector can be produced through transfection into an appropriate host to effect transformation, followed by culturing of thus obtained transformant. When the recombinant vector is a viral vector, animal cells capable of producing viruses are used as the host to be transfected with such a viral vector. For example, COS-7 cells, CHO cells, BALB/3T3 cells, and HeLa cells are use. Examples of the host to be used for retroviral vectors include ψCRE, ψCRIP, and MLV. Examples of the hosts to be used for adenoviral vectors or adeno-associated virus vectors include human embryonic kidney-derived 293 cells. Viral vectors can be transfected into animal cells by a calcium phosphate method. Moreover, when the recombinant vector is a vector for expression in animal cells, the *E. coli* K12 strain, the HB101 strain, and the DH5α strain, or the like can be used as the host to be transfected with such a vector. Transformation of *E. coli* is publicly known to those skilled in the art.

Thus obtained transformant is cultured in an appropriate medium under appropriate culture conditions, respectively. For example, a transformant of *E. coli* can be cultured using a liquid medium at a pH of about 5 to 8 containing carbon sources, nitrogen sources, inorganic substances, and the like which are essential for growth. The culture is normally carried out at 15° C. to 43° C. for about 8 to 24 hours. In this case, the recombinant vector of interest can be obtained through usual DNA isolation and purification methods, on completion of culture.

Moreover, transformants of animal cells can be cultured using a medium such as a 199 medium, an MEM medium, or a DMEM medium containing about 5% to 20% fetal bovine serum. The pH of the medium is preferably about 6 to 8. The culture is normally carried out at 30° C. to 40° C. for about 18 to 60 hours. In this case, since virus particles containing a target recombinant vector are released into a culture supernatant, the recombinant vector can be obtained through concentration and purification of the virus particles by a cesium chloride centrifugation method, a polyethylene glycol precipitation method, a concentration method using a filter, or the like.

The cell growth inhibitor of the present invention can be produced by mixing the abovementioned gene serving as an active ingredient with a base that is commonly used for gene therapeutic agents. Moreover, when such a gene is incorporated into a viral vector, virus particles containing the recombinant vector are prepared, and are then mixed with a base that is commonly used for gene therapeutic agents.

As to the base to be used for mixing the abovementioned gene or protein serving as an active ingredient, bases commonly used for injectable agents can be used. Examples thereof include: distilled water: salt solutions containing sodium chloride, a mixture of sodium chloride and mineral salts, or the like: solutions of mannitol, lactose, dextran, glucose, or the like: amino acid solutions of glycine, arginine, or the like: and mixed solutions having glucose solution with an organic acid or salt solution. Alternatively, these bases can also be prepared into injectable agents in the form of a solution, suspension, or dispersion, with use of auxiliary agents such as an osmoregulator, a pH adjuster, a vegetable oil, and a surfactant, in accordance with usual methods which are already known to those skilled in the art. These injectable agents can also be prepared in the form of a pharmaceutical preparation to be dissolved at the time of use, through operations such as powderization or lyophilization.

The form of administration of the cell growth inhibitor of the present invention may be either systemic administration such as usual intravenous administration and intraarterial administration, or local administration such as local injection and oral administration. Furthermore, administration of the cell growth inhibitor may also take a combined form with catheterization, gene introduction technology, or surgical operation.

The administration dose of the cell growth inhibitor of the present invention varies depending on the age and gender of the patient, the symptom, the administration route, the frequency of administration, and the dosage form. Generally, the daily dose for an adult is within a range of about 1 μg/kg of body weight to 1000 mg/kg of body weight, and preferably a range of about 10 μg/kg of body weight to 100 mg/kg of body weight, in terms of weight of recombinant gene. The frequency of administration is not particularly limited.

(5) Method for Activating Cell Growth and Cell Growth Activating Agent

According to the present invention, there are provided a method for activating cell growth which comprises introducing an siRNA, an shRNA, an antisense oligonucleotide, or a loss-of-function type gene of the KIAA1913, EPB42L2, AKAP7, CRSP3, ARG1, ENPP3, ENPP1 or CTGF gene into tumor cells in vitro, and a cell growth activating agent which comprises said siRNA, shRNA, antisense oligonucleotide, or loss-of-function type gene.

siRNA is a double-strand RNA having a length of about 20 nucleotides (for example, 21 to 23 nucleotides) or shorter. Expression of such an siRNA in a cell enables to suppress the expression of a gene targeted by the siRNA (KIAA1913, EPB42L2, AKAP7, CRSP3, ARG1, ENPP3, ENPP1 or CTGF gene in the present invention).

The siRNA to be used in the present invention may take any form as long as it is capable of inducing RNAi. Here, the term "siRNA" is an abbreviation for "short interfering RNA", which refers to a short-chain double-strand RNA of 10 nucleotides or longer obtained by: chemical or biochemical synthesis in an artificial manner; in vivo synthesis; or in vivo degradation of double-strand RNA of about 40 nucleotides or longer. The siRNA normally has a structure comprising 5'-phosphoric acid and 3'-OH, where the 3' terminal projects by about 2 nucleotides. A specific protein binds to the siRNA to form RISC (RNA-induced-silencing-complex). This complex recognizes mRNA having the homologous sequence to that of siRNA and binds thereto. Then, the mRNA is cleaved at the central part of the siRNA with an RNase III-like enzymatic activity.

The siRNA sequence and the mRNA sequence being the target of cleavage preferably match 100%. However, such 100% match is not always required, when unmatched nucleotides are located away from the central part of the siRNA. This is because the RNAi cleaving activity often partially remains.

Preferably, the homologous region between the siRNA nucleotide sequence and the nucleotide sequence of the KIAA1913, EPB42L2, AKAP7, CRSP3, ARG1, ENPP3, ENPP1 or CTGF gene whose expression has to be suppressed, does not include the translation initiation region of the concerned gene. Since various transcriptional factors and translational factors are predicted to bind to the translation initiation region, it is anticipated that the siRNA be unable to effectively bind to the mRNA, leading to lowered effect. Accordingly, the homologous sequence is preferably away from the translation initiation region of the concerned gene by 20 nucleotides, and more preferably by 70 nucleotides. The homologous sequence may be, for example, a sequence in the vicinity of the 3' terminal of the concerned gene.

According to another aspect of the present invention, an shRNA (short hairpin RNA) comprising a short hairpin structure having a projection at the 3' terminal may also be used as a factor which can suppress the expression of a target gene through RNAi. The term shRNA refers to a molecule of about 20 or more nucleotides, in which the single-strand RNA includes partially palindromic nucleotide sequences to thereby have a double-strand structure within the molecule, forming a hairpin-like structure. Such an shRNA is broken down into a length of about 20 nucleotides (typically 21 nucleotides, 22 nucleotides, and 23 nucleotides, for example) within a cell after being introduced into the cell, and thus is capable of inducing RNAi in a similar manner to that of siRNA. As described above, the shRNA induces RNAi in a similar manner to that of siRNA, and thus can be effectively used in the present invention.

The shRNA preferably has a projection at the 3' terminal. There is no particular limitation on the length of the double-strand portion, although it is preferably about 10 or more nucleotides, and more preferably about 20 or more nucleotides. Here, the projecting 3' terminal is preferably a DNA, more preferably a DNA of at least 2 or more nucleotides, and yet more preferably a DNA of 2 to 4 nucleotides.

As described above, in the present invention, siRNA or shRNA can be used as a factor which can suppress the expression of the KIAA1913, EPB42L2, AKAP7, CRSP3, ARG1, ENPP3, ENPP1 or CTGF gene through RNAi. The advantages of siRNA are such that: (1) RNA itself, even when introduced into a cell, is not incorporated into a chromosome of normal cell, and therefore the treatment do not cause any inheritable mutations and the safety is high; (2) it is relatively easy to chemically synthesize short-chain double-strand RNA, and the form of double-strand RNA is more stable; and the like. The advantages of shRNA are such that: treatment through long-term suppression of gene expression can be achieved by producing a vector which can transcribe shRNA within a cell and introducing such a vector into the cell; and the like.

The siRNA or shRNA to be used in the present invention which can suppress the expression of the KIAA1913, EPB42L2, AKAP7, CRSP3, ARG1, ENPP3, ENPP1 or CTGF gene through RNAi, may be chemically synthesized in an artificial manner, and may also be produced through in vitro RNA synthesis using DNA of a hairpin structure in which a sense strand DNA sequence and an antisense strand DNA sequence are linked in opposite directions, with a T7 RNA polymerase. In the case of in vitro synthesis, antisense and sense RNAs can be synthesized from a template DNA using the T7 RNA polymerase and a T7 promoter. After in vitro annealing thereof, transfection of the resultant RNA into cells induces RNAi to suppress the expression of a target gene. Here, for example, transfection of such RNA into cells can be carried out by a calcium phosphate method or a method using various transfection reagents (such as oligofectamine, lipofectamine, and lipofection).

The abovementioned siRNA and shRNA are also useful as cell growth activating agents. The administration method of the cell growth activating agent of the present invention may include oral administration, parenteral administration (such as intravenous administration, intramuscular administration, subcutaneous administration, intradermal administration, transmucosal administration, intrarectal administration, intravaginal administration, local administration to affected area, and skin administration), and direct administration to affected area. The agent of the present invention, if used as a medical composition, may be mixed with a pharmaceutically acceptable additive as required. Specific examples of such a pharmaceutically acceptable additive include, but not limited to, an antioxidant, a preservative, a coloring agent, a flavoring agent, a diluent, an emulsifier, a suspending agent, a solvent, a filler, an extending agent, a buffer agent, a delivery vehicle, a carrier, an excipient, and/or a pharmaceutical adjuvant.

The form of the pharmaceutical preparation of the agent of the present invention is not particularly limited, and examples thereof include a liquid agent, an injectable agent, and a sustained release agent. A solvent to be used for prescribing the agent of the present invention as the above pharmaceutical preparation may be either aqueous or non-aqueous.

Furthermore, the siRNA or shRNA serving as an active ingredient of the cell growth activating agent of the present invention can be administered in the form of a nonviral vector or a viral vector. In the case of a nonviral vector, there can be employed methods in which nucleic acid molecules are introduced using liposomes (such as a liposome method, an HVJ-liposome method, a cationic liposome method, a lipofection method, and a lipofectamine method), microinjection methods, methods in which nucleic acid molecules are transferred together with carriers (metal particles) into cells using a gene gun. If the siRNA or shRNA is administered in vivo using a viral vector, viral vectors such as a recombinant adenovirus and a recombinant retrovirus can be employed. Introduction of siRNA or shRNA gene into a cell or tissue can be achieved through introduction of DNA which expresses siRNA or shRNA into a detoxified DNA or RNA virus such as retrovirus, adenovirus, adeno-associated virus, herpes virus, vaccinia virus, poxvirus, poliovirus, Sindbis virus, Sendai virus, and SV40, followed by infection with the recombinant virus into the cell or tissue.

The dose of the cell growth activating agent of the present invention can be determined by those skilled in the art with a consideration of the purpose of administration, the disease severity, the age, weight, gender, and previous history of the patient, and the type of siRNA or shRNA serving as an active ingredient. The dose of siRNA or shRNA is not particularly limited, and examples thereof include about 0.1 ng/kg/day to about 100 mg/kg/day, and preferably about 1 ng/kg/day to about 10 mg/kg/day. RNAi effect is typically exerted for one to three days after the administration. Therefore, administration is preferably performed at a frequency of everyday to every third day. When an expression vector is used, the administration can be performed approximately once a week.

In the present invention, an antisense oligonucleotide can also be used as a cell growth activating agent. Antisense oligonucleotides to be used in the present invention are nucleotides that are complementary or hybridize to consecutive 5 to 100 nucleotide sequences within the DNA sequence of the KIAA1913, EPB42L2, AKAP7, CRSP3, ARG1, ENPP3, ENPP1 or CTGF gene. Such an antisense oligonucleotide may be either DNA or RNA, or may also be modified as long as its functions remain unaffected. The term "antisense oligonucleotide" used in this description includes not only oligonucleotides wherein all nucleotides corresponding to nucleotides composing a predetermined DNA or mRNA region are complementary to their counterparts, but also oligonucleotides that contain some mismatching nucleotides, as long as such oligonucleotides can stably hybridize to DNA or mRNA.

In addition, the antisense oligonucleotides may be modified. After appropriate modification, resulting modified antisense oligonucleotides will be hardly degraded in vivo. This enables more stable inhibition of ITIIα. Examples of such modified oligonucleotide include S-oligo type (phosphorothioate-type), C-5 thyazole type, D-oligo type (phosphodiester-type), M-oligo type (methylphosphonate-type), peptide nucleic acid type, phosphodiester binding type, C-5 propinyl pyrimidine type, 2-O-propylribose, and 2'-methoxyribose type antisense oligonucleotides. Furthermore, such antisense oligonucleotide may also be an antisense oligonucleotide wherein at least some of the oxygen atoms composing phosphate groups are substituted with sulfur atoms or otherwise modified. Such an antisense oligonucleotide is particularly excellent in terms of nuclease resistance, water solubility, and affinity for RNA. As such an antisense oligonucleotide wherein at least some of the oxygen atoms composing phosphate groups are substituted with sulfur atoms or otherwise modified, an S-oligo type oligonucleotide can be enumerated.

The number of nucleotides in such antisense oligonucleotide is preferably 50 or less and more preferably 25 or less. Too large number of nucleotides results in increased effort and cost in oligonucleotide synthesis and lowered yields. Furthermore, the number of nucleotides of such antisense oligonucleotide is 5 or more and preferably 9 or more. A number of nucleotides of 4 or less is undesirable because of the resulting lowered specificity to a target gene.

Such antisense oligonucleotide (or a derivative thereof) can be synthesized by a usual method. For example, an antisense oligonucleotide or a derivative thereof can be easily synthesized using a commercially available DNA synthesizer (such as one produced by Applied Biosystems). It can be obtained by a synthesis method such as a solid-phase synthesis method using phosphoroamidite or a solid-phase synthesis method using hydrogen phosphonate.

When an antisense oligonucleotide is used as a cell growth activating agent in the present invention, it is generally provided in the form of a medical composition containing the antisense oligonucleotide and additive(s) for pharmaceutical preparation (such as a carrier and an excipient). The antisense oligonucleotide can be administered as a medicament to mammals including humans. The route of administration for such an antisense oligonucleotide is not particularly limited and may be either of oral administration or parenteral administration (such as intramuscular administration, intravenous administration, subcutaneous administration, peritoneal administration, transmucosal administration in the nasal cavity or the like, and inhalation administration).

The form of the pharmaceutical preparation of such an antisense oligonucleotide is not particularly limited. Examples of the pharmaceutical preparation for oral administration include tablets, capsules, fine granules, powders, granules, liquids, and syrups. Examples of the pharmaceutical preparation for parenteral administration include injections, infusions, suppositories, inhalants, transmucosal absorption systems, transdermal absorption systems, nasal drops, and ear drops. The form of a drug containing the antisense oligonucleotide, additive(s) to be used for the pharmaceutical preparation, a method for producing the pharmaceutical preparation, and the like can be appropriately selected by those skilled in the art.

The dose of the antisense oligonucleotide can be appropriately determined with a comprehensive consideration of the gender, age, and weight of the patient, the symptom severity, the purpose of administration such as prevention or treatment, and the presence/absence of other complication symptoms. The dose is generally 0.1 μg/kg of body weight/day to about 100 mg/kg of body weight/day, and preferably 0.1 μg/kg of body weight/day to about 10 mg/kg of body weight/day.

Furthermore, in the present invention, a loss-of-function type gene of the KIAA1913, EPB42L2, AKAP7, CRSP3, ARG1, ENPP3, ENPP1 or CTGF gene can also be used as a cell growth activating agent. The loss-of-function type gene refers to a mutated gene which causes loss of function of the corresponding gene. Specific examples thereof include genes which translate proteins lacking their original functions, generally called muteins, including those lacking at least one constituent amino acid(s), those having at least one constituent amino acid(s) replaced by other amino acid(s), and those added with at least one amino acid(s), within the amino acid sequence produced by the concerned gene.

When such a loss-of-function type gene is used as the cell growth activating agent, it can be produced by mixing the abovementioned gene serving as an active ingredient with a base that is commonly used for gene therapeutic agents. Moreover, when such a gene is incorporated into a viral vector, virus particles containing the recombinant vector are prepared, and are then mixed with a base that is commonly used for gene therapeutic agents.

As to the base, bases commonly used for injectable agents can be used. Examples thereof include: distilled water: salt solutions containing sodium chloride, a mixture of sodium chloride and mineral salts, or the like: solutions of mannitol, lactose, dextran, glucose, or the like: amino acid solutions of glycine, arginine, or the like: and mixed solutions having glucose solution with an organic acid solution or salt solution. Alternatively, these bases can also be prepared into injectable agents in the form of a solution, suspension, or dispersion, with use of auxiliary agents such as an osmoregulator, a pH adjuster, a vegetable oil, and a surfactant, in accordance with usual methods which are already known to those skilled in the art. These injectable agents can also be prepared in the form of a pharmaceutical preparation to be dissolved at the time of use, through operations such as powderization or lyophilization.

The form of administration of the loss-of-function allele may be either systemic administration such as usual intravenous administration and intraarterial administration, or local administration such as local injection and oral administration. Furthermore, administration may also take a combined form with catheterization, gene introduction technology, or surgical operation.

The administration dose of the loss-of-function type gene varies depending on the age and gender of the patient, the symptom, the administration route, the frequency of administration, and the dosage form. Generally, the daily dose for an adult is within a range of about 1 μg/kg of body weight to 1000 mg/kg of body weight, and preferably a range of about 10 μg/kg of body weight to 100 mg/kg of body weight, in terms of weight of recombinant gene. The frequency of administration is not particularly limited.

Moreover, the abovementioned various gene therapeutic agents of the present invention can also be produced by adding a gene into a suspension of liposomes prepared by a usual method, followed by freezing and subsequent thawing. Examples of the method for preparing liposomes include a membrane shaking method, a sonication method, a reverse phase evaporation method, and a surfactant removal method. The suspension of liposomes is preferably subjected to sonication treatment before addition of a gene, so as to improve the efficiency of encapsulation of the gene. The liposomes having the gene encapsulated therein may be intravenously administered either directly or in the form of a suspension with water, physiological salt solution, or the like.

(6) Screening Method of Antitumor Substance

As described above, it is considered that inactivation of the KIAA1913, EPB42L2, AKAP7, CRSP3, ARG1, ENPP3, ENPP1 or CTGF gene serves as a main causative factor of ovarian cancer, and that drugs which normalize functions of such genes can be used as antitumor agents for ovarian cancer. In particular, if the causative factor of such inactivation is methylation of the CpG island of the CTGF gene, drugs capable of relieving/relaxing these causative factors are useful as antitumor agents.

As the premise for performing these present screening methods, ovarian cancer cells showing lowered expression level of the CTGF gene in specimen cells have to be obtained. In other words, the present screening method requires an "ovarian cancer cell line showing lowered expression of the CTGF gene due to methylation of CpG island of the CTGF gene". The method for establishing these cell lines can be carried out in accordance with usual methods, based on the abovementioned understandings. For example, such desirable "ovarian cancer cell line showing lowered expression of the CTGF gene due to methylation of CpG island of the CTGF gene (hereinunder, also referred to as methylated cancer cell line)" can be established by the following manner. Among at least cells exhibiting inactivation of the CTGF gene, cells showing restoration of the CTGF gene level by treatment with an already-known demethylating reagent (such as 5-azadeoxycytidine) are selected, and subjected to passage culture.

In the present screening method, test substances have to be contacted with the abovementioned methylated cancer cell line. The form of such contact is not specifically limited. The contact can be achieved by adding a test substance, preferably diluted at an appropriate dilution strength, to the culture product of the methylated cell line, and subsequent culturing thereof. The CTGF gene expression level in the methylated cancer cell line is quantified before and after addition of the test substance. Preferably, the quantification is performed with the passage of time. The difference in the gene expression level throughout the quantification is compared to that of a control culture product that has been cultured without addition of the test substance under the same condition. If the gene expression level of the culture product with addition of the test substance is higher than that of the control culture product, the test substance is selected as an "antitumor substance capable of activating the CTGF gene through demethylation of CpG island of the CTGF gene" in the reagent using a methylated cancer cell line.

Furthermore, preferably, the number of substances to be screened for as desirable antitumor ingredients for ovarian cancer by the present screening method is narrowed down to final candidates through additional in vivo screening, such as a screening method in which a growth inhibitory effect on ovarian cancer cells in nude mice transplanted with the abovementioned methylated cancer cell line, and improvement in the viability of such nude mice, are used as indexes.

The present invention is hereafter described in greater detail with reference to the following examples, although the technical scope of the present invention is not limited thereto.

EXAMPLES

Example 1

Gene Alteration in Ovarian Cancer

Figure 1:
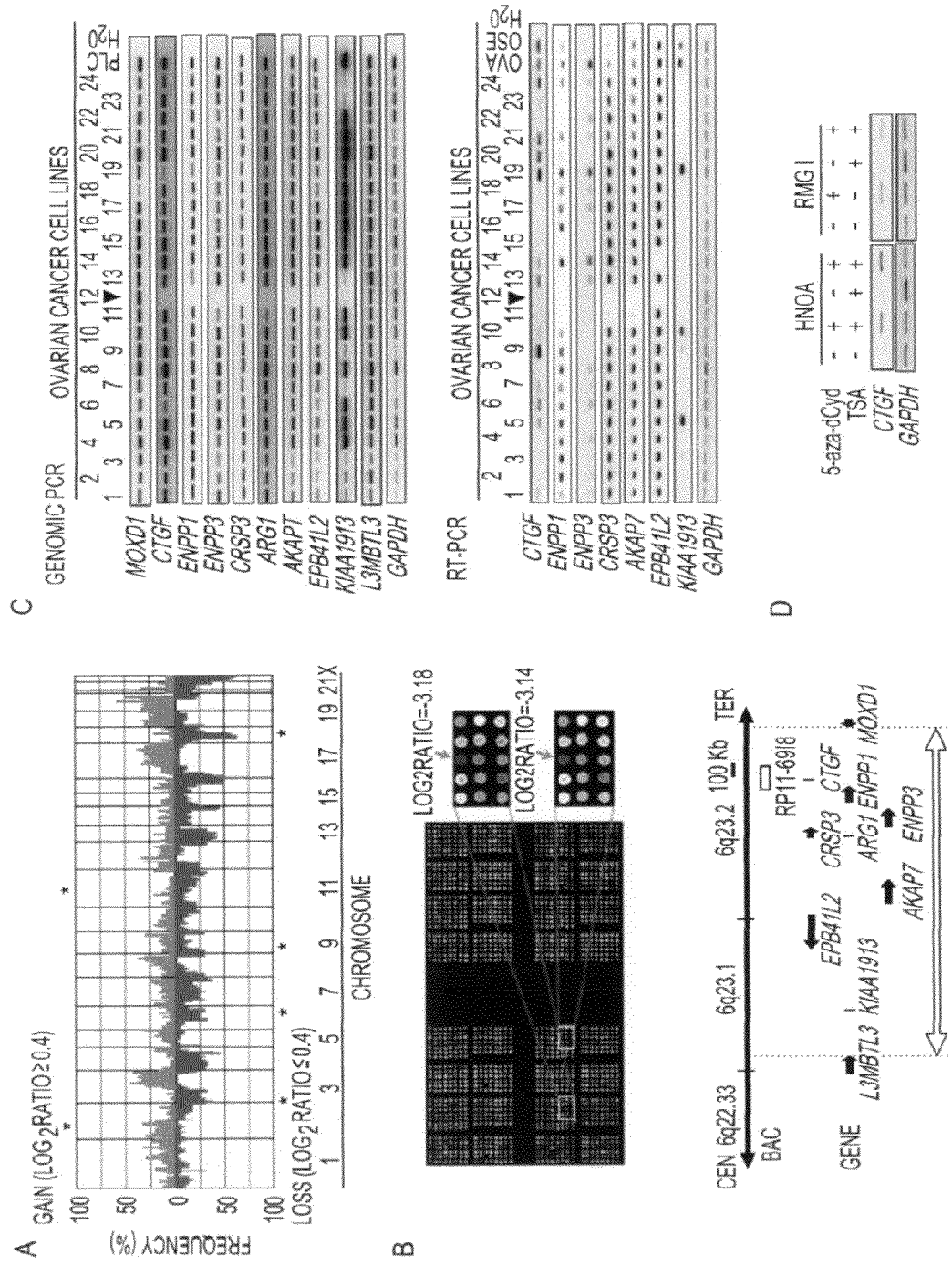
FIG. 1: A: Genome-wide frequencies of amplification and deletion of copy numberin 24 types of ovarian cancer cell line. Clones were aligned in order of chromosomes 1-22, X, and Y based on the UCSC mapping positions (http://genome.ucsc.edu/[version May, 2004]. Each asterisk represents a region for which high-level amplification (log 2 ratio>0.4) or homozygous deletion (log 2 ratio<−0.4) was observed (Table 1).

To detect a novel gene alteration in ovarian cancer, CGH array analysis was made using genomic DNAs prepared from 24 types of ovarian cancer cell line (HT, HTOA, HUOA, KF28, MH, OVTOKO, OVSAHO, KFr13, HMKOA, MCAS, RMUG-L, RMUG-S, KK, OVISE, OVMANA, OVTOKO, RMG-I, RMG-II, ES-2, W3UF, HIOAnu, HMOA, HNOA, and HTBOA), and using MGC Cancer Array-800 (FIG. 1a). A genome extracted from the cell line (OSE-2a) derived from normal ovarian epithelium was labeled with Cy5 as a control. Genomic DNAs prepared from the above ovarian cancer cell lines were used as test DNAs and labeled with Cy3. Specifically, each genomic DNA (0.5 µg) digested with Dpn II was labeled using a BioPrime Array CGH Genomic Labeling System (Invitrogen) in the presence of 0.6 mM dATP, 0.6 mM dTTP, 0.6 mM dGTP, 0.3 mM dCTP, and 0.3 mM Cy3-dCTP (ovarian cancer cells) or 0.3 mM Cy5-dCTP (normal cells). Cy3- and Cy5-labeled dCTPs were obtained from GE Healthcare. Ethanol was added so that the genomic DNA labeled with Cy3 or Cy5 was precipitated in the presence of Cot-1 DNA (Invitrogen). The resultant was dissolved in 120 µl of a hybridization mixture (50% formamide, 10% Dextran sulfate, 2×SSC (1×SSC: 150 mM NaCl/15 mM Sodium Citrate), 4% sodium dodecyl sulfate, pH 7.0). After 30 minutes of incubation at 37° C., the resultant was introduced onto a CGH array set in a hybridization machine (GeneTAC; Harvard Bioscience), followed by 48 to 72 hours of hybridization. Subsequently, the CGH array was washed in a 50% formamide/2×SSC (pH 7.0) solution at 50° C. for 15 minutes and then washed at 50° C. for 15 minutes in 2×SSC/0.1% SDS. After air-drying, the CGH array was monitored for fluorescence derived from Cy3 and Cy5 using GenePix 4000B scanner (Axon Instruments, CA, U.S.A.). The thus obtained results were analyzed using a GenePix Pro 6.0 imaging software (Axon Instruments, CA, U.S.A.). The average fluorescence intensity derived from Cy3 was adjusted to be the same as that of fluorescence intensity derived from Cy5, thereby determining the ratio of Cy3 to Cy5. When a genome has no abnormality, the resulting ratio is 1 (log 2 ratio=0). Determination was performed as follows. A ratio of 1.32 (or higher) (log 2 ratio=0.4 or more) indicates the presence of genome amplification and a ratio of 4 (or higher) (log 2 ratio=2.0 or more) indicates the confirmation of significant amplification. A ratio of 0.75 (or lower): 1 (log 2 ratio=−0.4 or less) indicates possible heterozygote deletion in the genome and a ratio of 0.25 (or lower): 1 (log 2 ratio=−2 or less) indicates an extremely high possibility of homozygote deletion in the genome. Table 1 and Table 2 show the results.

High-level gene amplification could be confirmed for 2 out of 24 types of ovarian cancer and in 2 gene loci. Moreover, gene deletion could be confirmed for 3 out of 24 types of ovarian cancer and in 4 gene loci (Table 1).

TABLE 1

Table 1 High-level amplifications (log2ratio > 2.0) and homozygous deletions (log2ratio < −2.0) detected in 24 ovarian cancer cell lines by arra-CGH analysis using MCG Cancer Array-800

| Alteration | BAC | Locus[a] Chr. Band | Position | Cell line (Total n = 24) n | Name | Known Candidate target gene[b] |
|---|---|---|---|---|---|---|
| High-level amplifications (log2ratio > 2.0) | RP11-438O12 | 2q14.2 | chr2: 120,629,082-120,846,427 | 1 | OVISE | GLI2 |
| | RP11-30016 | 11q13.3 | chr11: 69,162,462-69,323,966 | 1 | ES-2 | CCND1, FGF3 |
| | CTD-2234J21 | 11q13.3 | chr11: 69,307,612-69,307,884 | 1 | ES-2 | CCND1, FGF3 |
| Homozygous deletions (log2ratio < −2.0) | RP11-7116 | 3p24.1 | chr3: 30,541,893-30,705,070 | 1 | KFr13 | TGFBR2 |
| | RP11-69I8 | 8a23 | chr6: 132,249,163-132,410,700 | 1 | RMUG-S | none |
| | RP11-70L8 | 9p21.3 | chr9: 21,732,608-21,901,258 | 1 | HTBOA | CDKN2A, MTAP |
| | RP11-145E5 | 9p21.3 | chr9: 21,792,634-22,022,985 | 1 | HTBOA | CDKN2A, MTAP |
| | RP11-10I6 | 18q21.1 | chr18: 46,348,632-46,493,352 | 1 | RMUG-S | SMAD4 |

[a] Based on UCSC Genome Browser, May 2004 Assembly
[b] Putative oncogenes or tumor-suppressor genes located around BAC

TABLE 2

Supplemental Table S2 Most Frequently gained and lost clones in array-CGH analysis using MCG Cancer Array-800

| Alteration | Gene | Locus | Frequency (%)* |
|---|---|---|---|
| Gain | EVI1 | 3q26.2 | 46 |
| | MUC4 | 3q29 | 42 |
| | PTPN1 | 20q13.13 | 54 |
| | ZNF217 | 20q13.2 | 58 |
| | BCAS1 | 20q13.2 | 58 |
| | TFAP2C | 20q13.31 | 46 |
| | BIRC7 | 20q13.33 | 50 |
| | TNFRSF6B | 20q13.33 | 50 |
| Loss | VEGFC | 4q34.2 | 46 |
| | KLF12 | 13q22.1 | 42 |
| | FGF14 | 13q33.1 | 88 |
| | EFNB2 | 13q33.3 | 42 |
| | GABRB3 | 15q12 | 42 |
| | RAD51 | 15q15.1 | 46 |
| | RH68621 | 17p12 | 50 |
| | PMP22 | 17p12 | 46 |
| | RCV1 | 17p13.1 | 50 |
| | HSXIAPAF1 | 17p13.1 | 50 |
| | ABR | 17p13.3 | 50 |
| | HIC1 | 17p13.3 | 42 |
| | MADH4 (SMAD4) | 18q21.1 | 63 |
| | DCC | 18q21.2 | 58 |
| | MALT1 | 18q21.31 | 50 |
| | GRP | 18q21.32 | 63 |
| | SERPINB5/FVT1 | 18q21.33 | 58 |
| | BCL2 | 18q21.33 | 58 |
| | SERPINB3 | 18q21.33 | 50 |
| | BCL2/FVT1 | 18q21.33 | 42 |
| | CTDP1, SHGC-145820 | 18q23 | 54 |
| | SSX1 | Xp11.23 | 54 |
| | AR | Xq12 | 42 |
| | MLLT7 | Xq13.1 | 42 |
| | ABCB7 | Xq13.3 | 54 |
| | GPC3 | Xq26.2 | 58 |
| | FGF13 | Xq26.3 | 63 |
| | MAGEA2 | Xq28 | 63 |

*Alterations were defined by log2ratio thresholds of 0.4 and −0.4 for copy-number gain and loss, respectively. In this table, the gained and lost clones, which showed copy-number aberrations in above 40% of cell lines, were ordered according to chromosomal positions.

Example 2

Isolation of Gene Contained in Deletion Region of Chromosome 6q23 (6q23.1-23.2) of Ovarian Cancer To precisely determine a gene contained in a newly detected homozygous deletion region of chromosome 6q23 (6q23.1-23.2) in an ovarian cancer cell line (RMUG-S), the range of the homozygous deletion region was first determined by genomic PCR using genomic DNA extracted from RMUG-S cells as a template. Table 3 shows primer sequences (SEQ ID NOS: 1-48, forward then reverse primers, respectively) used in genomic PCR.

TABLE 3

Supplementary Table S1 Primer sequences used in this study

| Method | Target | Forward primer | Reverse primer |
|---|---|---|---|
| Genomic PCR | CTGF | 5'-TTCCAGAGCAGCTGCAAGTA | 5'-CTCGTCACACACCCACTCC |
| | MOXD1 | 5'-AAGGAAGGAAAGGCACACAA | 5'-TTTCCAAGGGGCTGGAGTAT |
| | ENPP1 | 5'-GCATGGAACAAGGCAGTTG | 5'-GGGACATCAGAGGGTCTCAA |
| | ENPP3 | 5'-AGGAGCACTAATTTATTCTGATAAAAC | 5'-GTGTTCTTCTTAACAGGTTGTTCC |
| | CRSP3 | 5'-AGGGAACGCTCCAGGTAAAG | 5'-CCTCTTCGAAAATGCTCTGC |
| | ARG1 | 5'-TTCCCTCTTGGTGTAAAATTCAA | 5'-GGGGGCTTATGTAAGTGTGC |
| | AKAP7 | 5'-CTTGCAGCGTGCTGTTTAAG | 5'-TGGGCCATTCTTCTTTCATC |
| | EPB41L2 | 5'-TCACACAGGTTTGAGGATGC | 5'-TAGGGTCAAAGGCAAAGGAA |
| | KIAA1913 | 5'-ATGAAACGTTTTTGCCCTTG | 5'-ACCTTTCCCAAACCTTTGCT |
| | L3MBTL3 | 5'-AGAGCGCTGTCTCAGGTCAT | 5'-AATCCTTCCAAAACGGAGGT |
| RT-PCR | CTGF | 5'-TTCCAGAGCAGCTGCAAGTA | 5'-CCAGGCAGTTGGCTCTAATC |
| | ENPP1 | 5'-CAGATCATGGCATGGAACAA | 5'-GGGACATCAGAGGGTCTCAA |
| | ENPP3 | 5'-GCAGCTACCAGGACAATGGA | 5'-GCAAGAAGAACAATGCAAGC |
| | CRSP3 | 5'-GGCAAACTTCCACACTGGTT | 5'-ATCCCTGGAATAAGGCTGCT |
| | AKAP7 | 5'-TCAGGATGACTGTGGAATCACT | 5'-TGAAAGGAACCATCACTGACC |

TABLE 3-continued

Supplementary Table S1 Primer sequences used in this study

| Method | Target | | Forward primer | Reverse primer |
|---|---|---|---|---|
| | EPB41L2 | | 5'-GGGGAAGATTAAGTAAGAAAGTCA | 5'-AGGTTTGGTGTTGGCATTTT |
| | KIAA1913 | | 5'-CAGCTGGTGTGTGCTAGAAGAG | 5'-CCACGAACAACCACAACATC |
| COBRA and Bisulfite Seqencing | CTGF | region 1 | 5'-GTAGGAAGGTGGGGAGGAA | 5'-CACTAACTATCTCCTCTCAAC |
| | | region 2-1st | 5'-GGAATGTTGAGTGTTAAGGGGTTAGGATTA | 5'-ATCAAACATTAAAACACTCTCACATCCAAA |
| | | region 2-nested | 5'-TTGAGAGGAGATAGTTAGTG | 5'-AACAAAATAAACCCTTATAC |
| | | region 3-1st | 5'-GGTTGTTAGGGAGGGATT | 5'-TCCATACTACACAAAAACATACAACC |
| | | region 3-nested | 5'-GTATAAGGGTTTATTTTGTTATTT | |
| MSP | CTGPMSP | | 5'-GGGTCGTGTCGGTGTTC | 5'-GTCCAACACGAAACTCACG |
| | CTGFUSP | | 5'-GTTGTGTTGGTGTTTGGAT | 5'-CATCCAACACAAAACTCACA |

Genes existing in the deletion region could be confirmed based on the results of CGH array and the human genome database (http://genome.ucsc.edu/) (FIG. 1B, FIG. 1C). As a result, the presence of 10 types of gene could be confirmed in the deletion region (FIG. 1B). Of these genes, homozygous deletion of the CTGF gene, the ENPP1 gene, the ENPP3 gene, the CRSP3 gene, the ARG gene, the AKAP7 gene, the EPB41L2 gene, and the KIAA1913 gene could be confirmed in RMUG-S cells (1/24, 4.2%; FIG. 1C).

Example 3

Disappearance of CTGF Gene Expression in Ovarian Cancer Cell Lines and Recovery After DNA Demethylation To examine the expression levels of the 7 above genes (the CTGF gene, the ENPP1 gene, the ENPP3 gene, the CRSP3 gene, the AKAP7 gene, the EPB41L2 gene, and the KIAA1913 gene), 24 types of ovarian cancer cell line, normal ovary, and a normal ovarian epithelial cell-derived immortalized cell line (OSE-2a) were subjected to reverse transcriptase (RT)-PCR. Specifically, a single-chain cDNA was synthesized from the RNA extracted from each cultured cell line using the SuperScript First-Strand Synthesis System (Invitrogen). PCR was then performed using primer sequences listed in Table 3. Moreover, a glyceraldehyde-3-phosphate dehydrogenase (GAPDH) gene was used as a control. As a result, decreased expression levels of the CTGF gene, the ENPP1 gene, and the KIAA1913 gene were shown, compared with the case of normal ovary or OSE-2a cells (FIG. 1D), although chromosomal region 6q23.1-23.2 had not undergone homozygous deletion. This may be due to a mechanism other than genomic deletion, such as an epigenetic phenomenon in ovarian cancer cell lines. Moreover, in the above experiment, the ARG1 gene was not subjected to examination, since the gene is not expressed in the ovary according to the results of analyzing the gene expression database (ncbi.Nlm.nih.gov and http://www.lsbm.org/database/index.html).

To examine if suppressed CTGF gene expression is due to DNA methylation, ovarian cancer cell lines (HNOA and RMG-II) not expressing the CTGF gene were treated using 5 μM demethylating reagent 5-aza-dCyd for 5 days or using deacetylation inhibitory agent TSA (100 ng/ml) for 12 hours. RNAs were extracted from these cells and then CTGF gene expression was examined by RT-PCR (FIG. 1D). As a result, it was revealed that the CTGF gene recovers its gene expression by treatment with 5-aza-dCyd. It was clearly assumed based on this result that DNA methylation is involved in suppression of the expression of the CTGF gene. Moreover, treatment with TSA resulted in no differences in CTGF gene expression. Hence, it was revealed that histone deacetylation lightly affects the regulation of CTGF gene expression.

Example 4

Methylation of the CpG Island of the CTGF Gene in Ovarian Cancer Cell Lines

Methylation of a CpG island is one mechanism that suppresses gene expression. The CpG island of the CTGF gene was analyzed using the CpGPLOT program (http://www.ebi.ac.uk/emboss/cpgplot/). As a result, the presence of the CpG island in the periphery of exon 1 or 2 of the CTGF gene was confirmed (FIG. 2A). To confirm the methylation status of the CpG island of the CTGF gene due to the presence or the absence of CTGF gene expression in ovarian cancer cell lines, bisulfite sequencing analysis was performed for 3 regions (Region 1, Region 2, and Region 3).

Specifically, with the use of an EZ DNA methylation kit (Zymo RESEARCH, CA, U.S.A.), genomic DNAs (2 μg each) derived from ovarian cancer cell lines were treated in sodium bisulfite at 50° C. overnight, and then PCR was performed using primers (Table 3) designed to amplify target regions. These sequences were each subcloned into a TOPO TA cloning vector (Invitrogen) and then the nucleotide sequence was determined. As a result, it could be confirmed that Region 2 and Region 3 were extremely methylated in cell lines (HTOA, HUOA, RMUG-L, RMG-I, HNOA, and KF28) with decreased levels of CTGF gene expression (FIG. 2A). Furthermore, methylation of the 3' portion of Region 2, methylation of Region 2B, and methylation of Region 3 could be confirmed also in cell lines (KK and OVISE) expressing the CTGF gene.

To further examine the correlation between the expression status and the methylation status of the CTGF gene in ovarian cancer cell lines, analysis was made using the COBRA method. Specifically, PCR products obtained by the above method were digested with a BstU I restriction enzyme (New England BioLabs) and then electrophoresed so as to perform detection. BstUI has a feature of not digesting an unmethylated sequence modified with sodium bisulfite, but digesting a methylated sequence not modified with sodium bisulfite. With the use of such feature, the degrees of methylation were monitored. After electrophoresis of PCR fragments, the ratio of the concentration of a band of a methylated fragment to that of a band of an unmethylated fragment was measured by densitometry using MultiGauge 2.0 (FUJIFILM Corporation). The degree of methylation of a methylated region was represented in percentage terms (FIGS. 2A and B). As a result, regardless of the expression status of the CTGF gene, no methylated alleles could be confirmed in Region 1 in most ovarian cancer cell lines (FIG. 2B). On the other hand, methylated alleles in Region 2 could be confirmed among ovarian cancer cells lacking CTGF gene expression other than in the cases of OVMANA cells and OVTOKO cells (FIG. 2B).

Example 5

Promoter Activity of Sequences in the Periphery of the CpG Island of the CTGF Gene To examine the promoter activity of the CpG island, the CpG island was divided into 3 fragments (Fragment 1, Fragment 2, and Fragment 3) including the peripheral portion thereof. These fragments were inserted into luciferase reporter plasmids (pGL3-Basic vector: Promega). Ovarian cancer cell lines (RMUG-S, KK, and KF28) were then transfected with the plasmids (FIG. 2C). Luciferase activity was measured according to the manuals using a Dual-Luciferase reporter assay system (Promega). Thus, luciferase activity derived from each pGL3 vector having each fragment was measured (FIG. 2C). As a result, Fragments 1 and 3 including Region 2A were found to have high luciferase activities (FIG. 3b). Based on the results of the above promoter assay, it was concluded that Region 2A methylation plays an important role in suppression of CTGF gene expression.

Example 6

Methylation of CTGF Promoter Region in Clinical Ovarian Cancer Specimen

To elucidate CTGF gene methylation in clinical ovarian cancer specimens, methylation-specific PCR (MSP) was performed using a primer set targeting a methylated site in the periphery of Region 2A in 66 types of clinical ovarian cancer specimens. The results are shown in FIG. 2D.

In accordance with the results of bisulfite sequencing and COBRA, methylation was confirmed in the cell line (RMUG-L) lacking CTGF expression, and unmethylation was confirmed in the cell line (OSE-2a) expressing CTGF (FIG. 2D). As a result, high-frequency CTGF methylation could be confirmed in 39 out of 66 types of clinical ovarian cancer specimens (59%, FIG. 2D). Furthermore, a tumor confirmed to experience no methylation by MSP analysis exhibited a low-frequency methylation pattern as a result of bisulfite sequencing, while a tumor confirmed to experience methylation by MSP analysis exhibited a high-frequency methylation pattern (FIG. 2D). To examine the correlation between CTGF methylation and gene silencing in clinical ovarian cancer specimens, CTGF mRNA expression status was confirmed by real-time RT-PCR using cDNAs prepared from 43 clinical ovarian cancer specimens. As a result, the gene expression levels were found to be sufficiently lower (P=0.041, Mann-Whitney U test, FIG. 2D) in cases in which methylation of CTGF Region 2A was confirmed by MSP than in cases in which no methylation was confirmed. It may be considered based on the results that methylation of CTGF Region 2A is associated with gene silencing. Furthermore, Table 4 shows the results of examining the correlation between methylation of the CTGF CpG island and clinicopathological diagnosis in 66 ovarian cancer cases.

TABLE 4

Supplemental Table S3 Correlation between clinical background and methylation of the CTGF Region2

| | Total n | Methylation of CTGF[a] n (%) | P-value[b] |
|---|---|---|---|
| Total | 66 | 39 (59) | |
| Age | | | |
| <60 years | 50 | 27 (54) | 0.077 |
| ≥60 years | 16 | 12 (75) | |
| FIGO stage | | | |
| I, II | 38 | 22 (58) | 0.818 |
| III, IV | 28 | 17 (61) | |
| Histotogic type | | | |
| Serous | 32 | 18 (56) | 0.876 |
| Mucinous | 8 | 6 (75) | |
| Clear cell | 17 | 11 (65) | |
| Endometrioid | 9 | 4 (44) | |
| Optimal surgery | | | |
| Optimal (<2 cm) | 54 | 31 (57) | 0.725 |
| Suboptimal (≥2 cm) | 9 | 6 (67) | |
| Unknown | 3 | 2 (67) | |
| Peritoneal Cytology | | | |
| Positive | 30 | 19 (63) | 0.920 |
| Negative | 29 | 18 (62) | |
| Unknown | 7 | 2 (29) | |
| Expression(IHC) | | | |
| Positive | 11 | 6 (55) | 0.739 |
| Negative | 44 | 27 (61) | |
| Unknown | 11 | 6 (55) | |

[a]Methylation status was determined by MSP target for Region2A described in Materials and Methods.
[b]P values are from $\chi^2$ or Fisher's exact test and were statistically significant when <0.05 (two-sided).

Example 7

Correlation Between CTGF Expression Levels and Clinicopathological Properties in Clinical Ovarian Cancer Specimens To clarify the clinical significance of the CTGF gene in ovarian cancer, the expression level of the CTGF protein in clinical ovarian cancer specimens was evaluated by immunohistochemical staining using a CTGF specific antibody. Specifically, paraffin-embedded tissue sections were fixed with formalin. Each section on a silane-coated glass slide was subjected to deparaffinization and stepwise dehydration using ethanol. An antigen was obtained by pre-autoclaving performed at 95° C. for 10 minutes in a high-pH buffer (Dako Cytomation, Target Retrieval Solution High pH). Endogenous peroxidase was inhibited using 5% hydrogen peroxide. Non-specific staining was inhibited using 2% standard pig serum. The slides were incubated overnight at 4° C. using an anti-human CTGF goat polyclonal antibody (L-20, 1:100 dilution; Santa Cruz Biotechnology). The slides were allowed to react at room temperature for 2 hours using Histofine Simple Stain MAX PO(G) (Nichrei). Antigen-antibody reaction was visualized using 0.2% diaminobenzidine tetrahydrochloride and hydrogen peroxide. The slides were subjected to contrast staining using Mayer's hematoxylin.

The results of immunohistological staining were classified into level 0 (negative staining), level 1 (1% to 10% of tumor cells were stained), level 2 (10% to 50% of tumor cells were stained), and level 3 (50% or more of tumor cells were stained). High-level CTGF immune reaction could be confirmed in normal ovarian epithelium (left, FIG. 3A). CTGF protein was revealed to be dominantly localized in the cell membranes or cytoplasms of normal or neoplastic epithelial cells.

High CTGF expression levels were detected in some ovarian cancer samples (center, FIG. 3A); however, weak (level 1) or no (level 0) CTGF expression could be frequently confirmed also in ovarian cancer samples (right, FIG. 3A). 81% (46 out of 57 cases) of ovarian cancer samples showed low CTGF expression levels (levels 0 and 1) and 19% (11 out of 57 cases) of the same showed high expression levels (levels 2 and 3). Table 5 collectively shows the correlation between CTGF protein expression levels and clinicopathological properties. The results revealed the existence of correlation between CTGF protein expression and tumor stages. Tumors lacking CTGF expression tend to be at low tumor stages (Stages I and II), and tumors presenting CTGF expression tend to be at high tumor stages (Stages III and IV).

TABLE 5

Table 2 Correlation between clinical background and expression of CTGF protein

|  | Total n | Expression of CTGF$^a$ n(%) | P-value$^b$ |
| --- | --- | --- | --- |
| Total | 57 | 11 (19) |  |
| Age |  |  |  |
| <60 years | 42 | 10 (24) | 0.256 |
| ≥60 years | 15 | 1 (7) |  |
| FIGO stage |  |  |  |
| I, II | 37 | 4 (11) | 0.038 |
| III, IV | 20 | 7 (35) |  |
| Histologic type |  |  |  |
| Serous | 23 | 4 (17) | 0.230 |
| Mucinous | 8 | 4 (50) |  |
| Clear cell | 17 | 1 (6) |  |
| Endometrioid | 9 | 2 (22) |  |
| Optimal surgery |  |  |  |
| Optimal (<2 cm) | 47 | 9 (19) | 1.000 |
| Suboptimal (≥2 cm) | 7 | 1 (14) |  |
| Unknown | 3 | 1 (33) |  |
| Peritoneal Cytology |  |  |  |
| Positive | 24 | 6 (25) | 0.518 |
| Negative | 29 | 5 (17) |  |
| Unknown | 4 | 0 (0) |  |
| Methylation$^c$ |  |  |  |
| Positive | 33 | 6 (18) | 0.739 |
| Negative | 22 | 5 (23) |  |
| Unknown | 2 | 0 (0) |  |

NOTE:
Statistically significant values are in boldface type.
$^a$CTGF protein expression was evaluated by immunohistochemical analysis described in Materials and Methods.
$^b$P values are from $\chi^2$ or Fisher's exact test and were statistically significant when <0.05 (two-sided).
$^c$Methylation status was determined by MSP target for Region2A described in Materials and Methods.

Regarding the overall survival rate, ovarian cancer patients showing low CTGF protein expression levels exhibited higher survival rates than patients showing high CTGF protein expression levels (P=0.128, Log-rank test; left, FIG. 3B). In the cases of Stages I and II, the lower the CTGF protein expression level, the lower the survival rate (center, FIG. 3B). Moreover, in the cases of Stage III and IV, the higher the CTGF protein expression level, the lower the survival rate (P=0.189, Log-rank test; right, FIG. 3B).

Such tendencies appear clearer when cases were limited to cases of stages IIIc and IV under the age of 60 (=<60) associated with a metastatic phenotype (P=0.033, Log-rank test; FIG. 3C). Accordingly, the role of CTGF inactivation in tumorigenesis may differ in different ovarian cancer stages.

Example 8

Suppression of Ovarian Cancer Proliferation by Activation of the CTGF Gene

It was examined based on these results whether activation of CTGF gene expression resulted in suppression of proliferation of ovarian cancer. First, a plasmid (pCMV-3Tag4-CTGF) expressing the Myc tag of the CTGF gene was constructed. This can be used for monitoring the role of the full-length CTGF gene. This plasmid was prepared by inserting CTGF cDNA amplified by RT-PCR into a pCMV-3Tag4 vector (Stratagene) so that the Myc tag matched the translation frame. An empty vector (pCMV-3Tag4-mock) in which no CTGF gene had been inserted was used as a control. These expression plasmids were mixed with a transfection reagent, FuGENE6 (Roch Diagnostics). HNOA or HMOA cells were transfected with the plasmids. Cells were collected after 48 hours and then subjected to Western blot analysis using an anti-Myc antibody (Cell Signaling Technology). Thus, CTGF protein expression was confirmed (FIG. 4A).

On week 2 after transfection, cells that had proliferated in the presence of a neomycin-based drug, G418, were fixed with 70% ethanol, stained with crystal violet, and then counted. As a result, the colony count of the cells transfected with pCMV-3Tag4-CTGF significantly decreased compared with that of the cells transfected with the empty vector (FIG. 4B). The results clearly demonstrate that the proliferation of ovarian cancer can be suppressed through activation of CTGF gene expression and that CTGF can function as an anticancer agent.

Effect of the Invention

According to the present invention, it becomes possible to precisely understand signs of canceration and malignancy in an ovary-derived cell specimen. Furthermore, proliferation of ovarian cancer can be suppressed by introducing a transcript of the CTGF gene that inactivates the gene expression in ovarian cancer. Furthermore, a therapeutic agent for ovarian cancer that is developed by inactivation of CTGF gene expression can be screened.

The invention claimed is:

1. A method for inhibiting cell growth of ovarian cancer cells, which comprises introducing, into ovarian cancer cells in vitro, a nucleic acid encoding a CTGF protein, or a CTGF protein.

2. The method according to claim 1, wherein the ovarian cancer cells are HNOA or HMOA cells.

* * * * *